(12) United States Patent  (10) Patent No.: US 8,337,380 B2
Ellingboe et al.  (45) Date of Patent: Dec. 25, 2012

(54) MULTI-UNIT BLOOD PROCESSOR WITH ROTATING VALVES

(75) Inventors: Bruce Ellingboe, Littleton, CO (US); Hong Duc Nguyen, Lafayette, CO (US)

(73) Assignee: Terumo BCT, Inc., Lakewood, CO (US)

( * ) Notice: Subject to any disclaimer, the term of this patent is extended or adjusted under 35 U.S.C. 154(b) by 232 days.

(21) Appl. No.: 12/941,538

(22) Filed: Nov. 8, 2010

(65) Prior Publication Data

US 2011/0136645 A1  Jun. 9, 2011

Related U.S. Application Data

(60) Provisional application No. 61/267,484, filed on Dec. 8, 2009.

(51) Int. Cl.
*B04B 7/08* (2006.01)
(52) U.S. Cl. .................................. 494/45; 494/5; 251/7
(58) Field of Classification Search ............... 494/5, 43, 494/45; 215/4, 7–10
See application file for complete search history.

(56) References Cited

U.S. PATENT DOCUMENTS

| | | |
|---|---|---|
| 6,910,998 B2 | 6/2005 | Eberle |
| 7,166,217 B2 | 1/2007 | Holmes et al. |
| 2006/0145105 A1* | 7/2006 | Ishida et al. ..................... 251/7 |
| 2008/0147240 A1 | 6/2008 | Hudock et al. |

FOREIGN PATENT DOCUMENTS

| | | |
|---|---|---|
| EP | 1607111 B1 | 5/2000 |
| EP | 1757318 B1 | 8/2006 |

OTHER PUBLICATIONS

U.S. Appl. No. 12/769,255, filed Apr. 28, 2010, Dolecek, Victor.
U.S. Appl. No. 12/813,952, filed Jun. 11, 2010, Dolecek, Victor.
PCT/US2010/055770, "International Search Report", mailed Dec. 2, 2011.
PCT/US2010/055770, "Written Opinion", mailed Dec. 2, 2011.

* cited by examiner

*Primary Examiner* — Walter D Griffin
*Assistant Examiner* — Timothy Cleveland
(74) *Attorney, Agent, or Firm* — John R. Merkling

(57) ABSTRACT

An apparatus for separating at least two discrete volumes of a composite liquid into at least a first component and a second component, comprising a valve design that facilitates loading and unloading of blood bags and associated tubing and bag sets. The valves comprise a rotating head, mounted on a shaft, which assumes a "load" position. The head pivots to an "open" position, which secures the tube in its designated location, but which maintains an open lumen through the tube. When the head is in a "closed" position, blood components cannot flow through the tube. The valve apparatus comprises means for maintaining a constant pressure on the tube and contact with the tube as the tube is melted and sealed.

13 Claims, 8 Drawing Sheets

MULTI-UNIT BLOOD PROCESSOR WITH ROTATING VALVES

CROSS REFERENCE TO RELATED APPLICATIONS

This application claims the benefit of U.S. Provisional Application No. 61/267,484 filed Dec. 8, 2009.

FIELD OF THE INVENTION

The present invention relates to an apparatus and a method for separating at least two discrete volumes of a blood into at least two components each.

BACKGROUND

U.S. Pat. No. 7,674,221 describes an apparatus for separating discrete volumes of a composite liquid such as blood into at least two components.

The apparatus and a method of the invention are particularly appropriate for the separation of biological fluids comprising an aqueous component and one or more cellular components. Potential uses of the invention include: extracting a plasma component and a cellular component (including platelets, white blood cells, and red blood cells) from a volume of whole blood. A component, such as washed red blood cells, may also be filtered so as to remove residual prions, white blood cells or platelets from the red blood cells.

An apparatus for processing blood components that can process at once at least two discrete volumes of a composite liquid, in particular, two unequal volumes wherein the proportions of the various components of the composite liquid that may vary from one discrete volume to another one, is known from U.S. Pat. No. 7,674,221. A method is described therein for separating at least two discrete volumes of a composite liquid into at least a first component and a second component. The method comprises at least two separation bags containing two discrete volumes of a composite liquid in separation cells mounted on a rotor; storing in at least one container on the rotor at least two first component bags connected to the at least two separation bags respectively; separating at least a first and a second components in each of the separation bags; transferring at least one fraction of a first separated component into a component bag; detecting a characteristic of a component at a location in each separation bag; and stopping transferring the fraction of the first component upon detection of the characteristic of a component at the first determined location.

SUMMARY OF THE INVENTION

The present invention comprises improvements on a centrifugal blood separation device capable of processing a plurality of blood units at the same time. The improvements include a valve design that facilitates loading and unloading of blood bags and associated tubing and bag sets. The valves of this invention comprise a rotating head, mounted on a shaft, which assumes a "load" position that allows a tube of the disposable set to be rapidly and securely inserted into a designated location on the rotor. The head pivots to an "open" position, which secures the tube in its designated location, but which maintains an open lumen through the tube, whereby blood or a blood component can flow through the tube. The head may also be drawn into a "closed" position from time to time. When the head is in the closed position, blood or blood components cannot flow through the tube. The head may also convey radio frequency energy to the tube to seal and sever the tube. The valve apparatus comprises means for maintaining a constant pressure on the tube and contact with the tube as the tube is melted and sealed. The constant pressure means may comprise a pre-loaded spring or similar structure, such as a pre-loaded pneumatic actuator. The valve may mechanically and electrically disconnect the shaft and head from a stepper motor during radiofrequency (RF) welding that seals the tube.

In addition, an asymmetrical junction in the blood bag and tubing set inhibits errors when the bags and tubings are loaded into the device. Further, a well is provided on a rotor near the axis of rotation for receiving a relatively rare blood component, such as mesenchymal stem cells (MSC) or another component, or for receiving a fluid that can be used multiple times, such as a washing solution. The well is positioned such that the processing bag is located in a relatively high force region of the centrifugal field produced by the rotation of the rotor, while the component bags are located in a lower force region, and a small bag placed in the well would be in the lowest force region. By reason of bag placement in high, intermediate and low force regions of the centrifugal field, air will tend to collect in the small bag in the well. Moreover, a shorter line or tube can be used to connect the small bag to the entire bag assembly. The three placement zones aides in simplifying the bag assembly and makes the process of loading the bag assembly into the rotor easier.

According to the present invention, an apparatus is provided for separating at least two discrete volumes of a composite liquid into at least a first component and a second component, the apparatus comprising a centrifuge having a rotor with a rotation axis, at least two separation cells mounted on the rotor, each cell adapted to receive a separation bag containing a volume of composite liquid, such as blood; and at least one sensor associated with each separation cell for generating information related to a characteristic of a component separated in a separation bag within the separation cell; and a control unit programmed for receiving information generated by the at least one sensor associated with each separation cell; and for controlling rotation speed in view of information generated by one of the at least one sensor associated with each of the at least two separation cells. The apparatus is adapted to receive a disposable set of tube-connected bags. The disposable set preferably comprises a primary bag, initially containing whole blood, fluidly connected to at least one (preferably two) component bag for receiving blood components such as plasma or platelets. A discard bag may also be provided. The disposable set may further comprise a red blood cell collection bag fluidly connected to the primary bag through a filter.

The apparatus comprises a plurality of valves associated with each separation cell. The valves comprise at least one valve adapted to control fluid flow into the at least one component bag, more preferably two valves where two component bags are provided, each component valve being associated with a component bag. The valves may further comprise a discard valve for controlling fluid flow of used wash solution into the wash solution discard bag.

The disposable set comprises an asymmetrical junction joining a plurality of tubes of the bag set. The asymmetrical junction can be mounted on the rotor (which carries the valves) in a single orientation only. Such an action brings the tubes of the disposable set into proximity with appropriate valves. The bag set can be quickly and unambiguously mounted on the apparatus with less potential for operator error.

Further, a well may be provided on a central part of the rotor, adjacent the valves. The well is adapted to receive a blood component or waste product bag, The bag, being mounted near the axis of rotation of the rotor of the apparatus, may be drained into other bags of the set one or more times. For example, a washing fluid may be used multiple times to reduce the presence of unwanted cell types or other particles in a collected blood component.

The well may be positioned such that the processing bag is located in a relatively high force region of the centrifugal field produced by the rotation of the rotor, while the component bags are located in a lower or intermediate force region, and a small bag placed in the well would be in the lowest force region or low force region. Air will tend to collect in the small bag in the well and a shorter line or tube can be used to connect the small bag to the entire bag assembly. The three placement zones aides in simplifying the bag assembly and makes the process of loading the bag assembly into the rotor easier.

Other features of the apparatus include a control unit programmed for causing the rotor to rotate at a sedimentation speed for separating a least two components in at least two primary or separation bags contained in the at least two separation cells respectively; causing at least one valve associated with each separation cell to allow a flow of fluid between each separation bag and the component bag connected thereto; causing the component transferring means to transfer at least a portion of a separated component from each of the at least two separation bags into the component bag connected thereto; and causing at least one valve associated with each separation cell to block a flow of fluid between the separation bag within the separation cell and the component bag connected thereto, when the sensor associated with the separation cell detects the characteristic of a separated component. The control unit may also slow the rotor, cause hydraulic fluid to be pulled from bladders adjacent the primary bags, and open wash valves thereby allowing wash solution to flow into the primary bag. The control unit then causes additional hydraulic fluid to be withdrawn from the bladders, whereby a free fluid surface is created within the primary bag. The control unit may cause the rotor to oscillate, thereby agitating the residual blood component and wash solution within the primary bag, and then causes the rotor to rotate at a sedimentation speed for separating the residual blood component and the wash solution. The control unit causes the wash solution discard valve to open, allowing used wash solution to flow into the wash solution discard bag. The residual blood component may be washed a plurality of times, thereby reducing levels of a cellular component or other components such as prions to a medically acceptable level.

Other features and advantages of the invention will appear from the following description and accompanying drawings, which are to be considered exemplary only.

DESCRIPTION OF EMBODIMENT

For the sake of clarity, the invention will be described with respect to a specific use, namely the separation of whole blood into at least two components, in particular into a plasma component and a red blood cell component, or into a plasma component, a platelet component and a red blood cell component. The discrete volume mentioned hereunder will typically be the volume of a blood donation. The volume of a blood donation may vary from one donor to another one (for example, 500 ml plus or minus 10% in the United States). It is also recalled that the proportion of the components of blood usually varies from one donor to another one. In particular, the donor's hematocrit, which is the ratio of the volume of the red blood cells to the volume of the sample of whole blood considered, varies from one person to another. In other words, the density of blood may slightly vary for one donor to another one. It should be understood however that this specific use is exemplary only.

Figure 1:
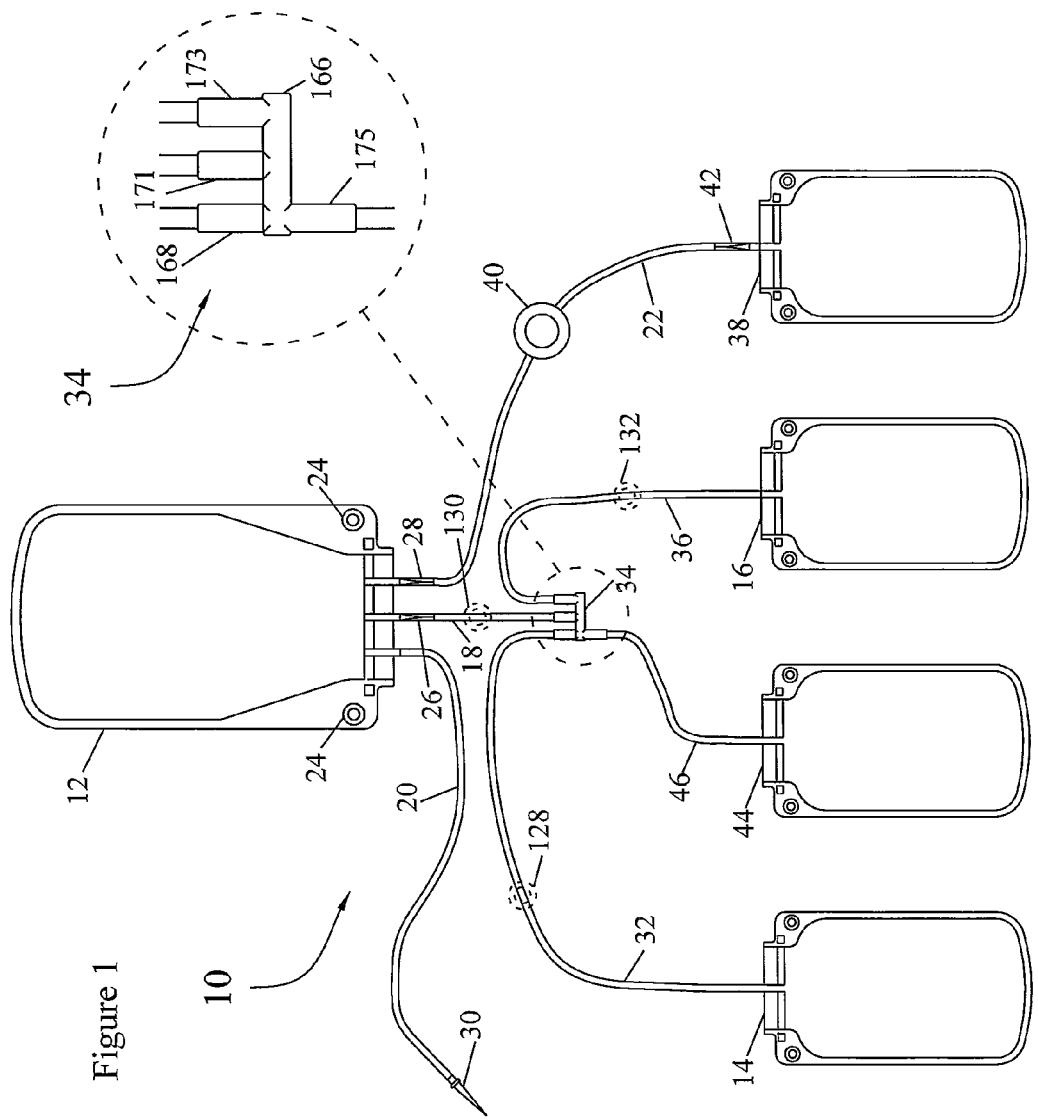
FIG. 1 is a schematic view of a first set of bags designed for cooperating with a separation apparatus.

FIG. 1 shows an example of a set 10 of bags adapted to be used for the separation of a composite liquid (e.g. whole blood) into at least one component (e.g. plasma, platelets, or both) and a second component (e.g. red blood cells). This bag set comprises a flexible primary separation bag 12 and two flexible component bags 14, 16 connected thereto.

When the composite liquid is whole blood, the separation bag 12 has two purposes, and is successively used as a collection bag and as a separation bag. It is intended to initially receive a discrete volume of whole blood from a donor (usually about 500 ml) and to be used later as a separation chamber in a separation apparatus. The separation bag 12 is flat and generally rectangular. It is made of two sheets of plastic material that are welded together so as to define there between an interior space having a main rectangular portion connected to a triangular proximal portion. A first tube 18 is connected to a proximal end of the triangular portion, and a second tube 20 and a third tube 22 are connected on opposite sides adjacent the first tube 18. The proximal ends of the three tubes 18, 20, 22 are embedded between the two sheets of plastic material so as to be parallel. The separation bag 12 further comprises a hole 24 in each of its two proximal corners that are adjacent to the three tubes 18, 20, 22. The holes 24 may be used to secure the separation bag to a separation cell on a centrifugal blood separation apparatus.

The separation bag initially contains a volume of anticoagulant solution (typically about 63 ml of a solution of citrate phosphate dextrose for a blood donation of about 450 ml). The first and third tubes 18, 22 are fitted at their proximal ends with a breakable stopper 26, 28 respectively, blocking liquid flow therethrough. The breakable stopper is sometimes called a "frangible". The second tube 20 is a collection tube having a needle 30 connected to its distal end. At the beginning of a blood donation, the needle 30 is inserted in the vein of a donor and blood flows into the separation bag 12. After a desired volume of blood has been collected in the separation bag 12, the collection tube 20 is sealed and cut, disconnecting the needle from the bag set 10. Alternatively, previously collected blood may be transferred to the separation bag 12 through the collection tube 20, with or without the use of the needle 30.

The first component bag 14 is intended for receiving a plasma component. The bag 14 is flat and substantially rectangular. It is connected through a plasma collection tube 32 and an asymmetric manifold 34 to the first tube 18. The second component bag 16 is intended for receiving a platelet component. The second component bag 16 is also flat and substantially rectangular. It is connected through a platelet collection tube 36 and the asymmetric manifold 34 to the first tube 18. A third component bag 38 is intended to receive a red blood cell component (which may be washed), from the primary bag 12. Red blood cells may be drained through tube 22, which may include a filter 40, into third component bag 38. A breakable stopper 42 or frangible in tube 22 prevents premature flow of red blood cells into the third component bag 38.

A wash solution bag 44, if used, may initially contain wash solution such as saline or a storage solution such as SAGM. Wash solution may be transferred through a wash solution tube 46 and the asymmetrical manifold 34 by way of the first tube 18 into the primary bag 12 when the primary bag 12 contains high hematocrit red blood cells. "High hematocrit" means a percentage of red blood cell volume to total fluid volume of at least 80 percent, more preferably 90 percent, and yet more preferably 95 percent. After wash solution is mixed with high hematocrit red blood cells and subsequently separated, used wash solution may be extracted through the first tube 18, asymmetrical manifold 34, and discard tube 46 into a wash solution discard bag 44. The discard bag 44 could also be used to collect a relatively rare blood component, for example, mesenchymal stem cells or some white cells to reduce filter load.

Figure 2:
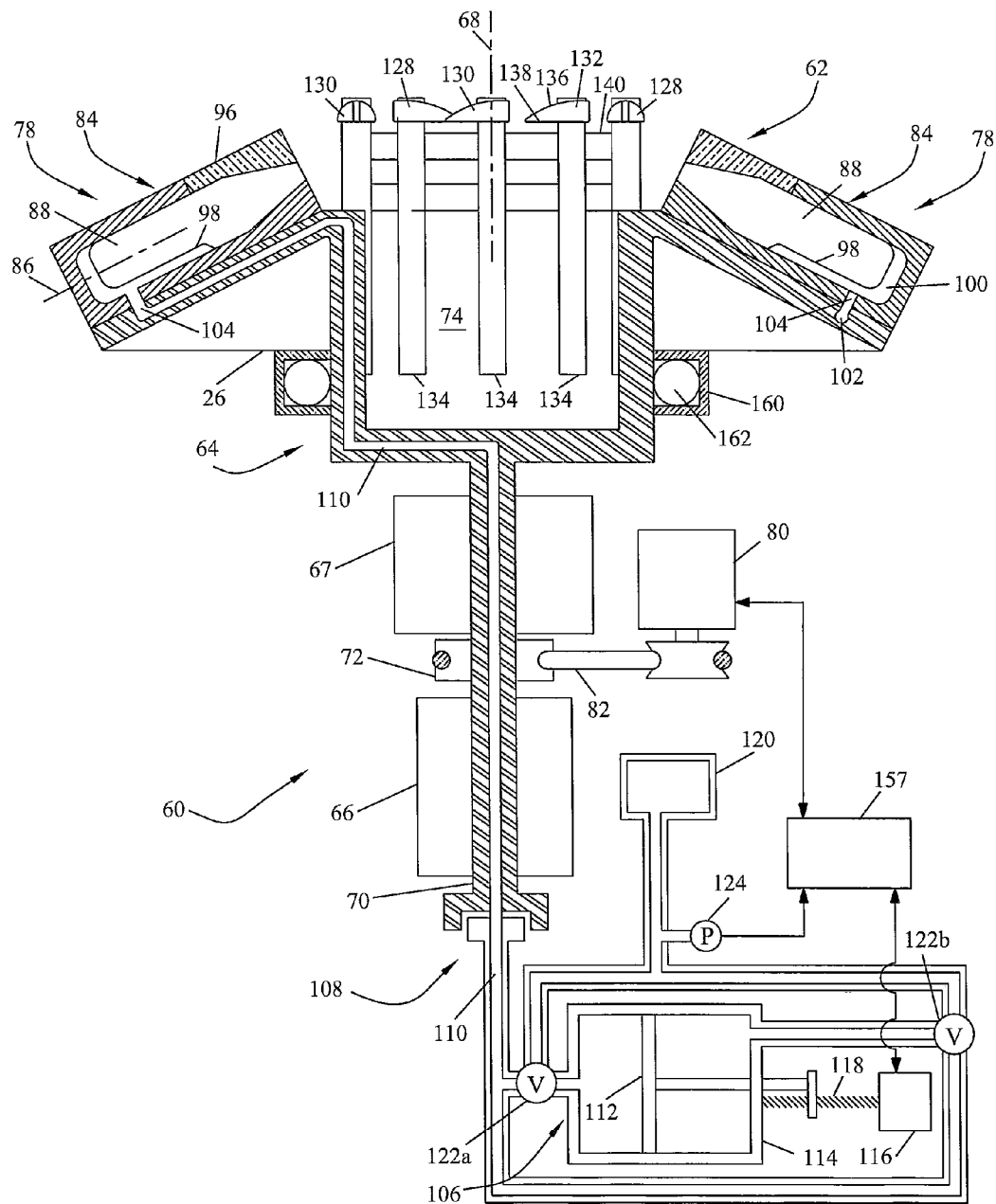
FIG. 2 is a schematic view, partly in cross-section along a diametric plane, of a first embodiment of a separation apparatus.

FIG. 2 shows a first embodiment of an apparatus 60 for simultaneously separating by centrifugation four discrete volumes of a composite liquid. The apparatus comprises a centrifuge 62 adapted to receive four of the sets 10 of bags shown in FIG. 1, with the four discrete volumes of a composite liquid contained in the four primary separation bags 12; a component transferring means for transferring at least one separated component from each separation bag into a component bag connected thereto. The apparatus 60 may further comprise means for washing a residual high hematocrit red blood cell component.

The centrifuge 62 comprises a rotor 64 that is supported by a bearing assembly 67 allowing the rotor 64 to rotate around a rotation axis 68. The rotor comprises a cylindrical rotor shaft 70 to which a pulley 72 is connected; a storage means comprising a central cylindrical container 74 for containing component bags, which is connected to the rotor shaft 70 at the upper end thereof so that the longitudinal axis of the rotor shaft 70 and the longitudinal axis of the container 74 coincide with the rotation axis 68. Four identical separation cells 78 are coupled to the central container 74 so as to form a symmetrical arrangement with respect to the rotation axis 68. The centrifuge further comprises a motor 80 coupled to the rotor by a belt 82 engaged in a groove of the pulley 72 so as to rotate the rotor about the rotation axis 68.

Each separation cell 78 comprises a container 84 having the general shape of a rectangular parallelepiped. The separation cells 78 are mounted on the central container 74 so that their respective median longitudinal axes 86 intersect the rotation axis 68, so that they are located substantially at the same distance from the rotation axis 68, and so that the angles between their median longitudinal axes 86 are substantially the same (i.e. 90 degrees). The median axes 86 of the separation cells 78 are inclined downwardly with respect to a plane perpendicular to the rotation axis 68.

Each container 84 comprises a cavity 88 that is so shaped and dimensioned as to loosely accommodate a separation bag 12 full of liquid, of the type shown in FIG. 1. The cavity 88 (which will be referred to later also as the "separation compartment") is defined by a bottom wall, which is the farthest to the rotation axis 68, a lower wall that is the closest to the container 74, an upper wall opposite to the lower wall, and two lateral walls. The cavity 88 comprises a main part, extending from the bottom wall, which has substantially the shape of a rectangular parallelepiped with rounded corners and edges, and an upper, or proximal, part, which has substantially the shape of a prism having convergent triangular bases. In other words, the upper part of the cavity 88 is defined by two sets of two opposing walls converging towards the central median axis 86 of the container 84. One interesting feature of this design is that it causes a radial dilatation of a thin layer of a minor component of a composite fluid (e.g. the platelets in whole blood) after separation by centrifugation, and makes the layer more easily detectable in the upper part of a separation bag. This also reduces mixing between component layers by providing a gradual, funnel-like transition into the tube. The two couples of opposite walls of the upper part of the separation cell 78 converge towards three cylindrical parallel channels (not shown), opening at the top of the container 84, and through which, when a separation bag 12 is set in the container 84, the three tubes 18, 20, 22 extend.

The container 84 also comprises a hinged lateral lid 96, which is comprised of an upper portion of the external wall of the container 84. The lid 96 is so dimensioned as to allow, when open, an easy loading of a separation bag 12 full of liquid into the separation cell 78. The container 84 comprises a locking means (not shown) by which the lid 96 can be locked to the remaining part of the container 84. The container 84 also comprises a securing or locating means for securing or locating a separation bag 12 within the separation cell 78. The bag securing or locating means comprises two pins (not shown) protruding on the internal surface of the lid 96, close to the top of separation cell 78, and two corresponding recesses in the upper part of the container 84. The two pins are so spaced apart and dimensioned as to fit into the two holes 24 in the upper corners of a separation bag 12.

The separation apparatus further comprises a component transferring means for transferring at least one separated component from each separation bag into a component bag connected thereto. The component transferring means comprises a squeezing system for squeezing the separation bags 12 within the separation compartments 88 and causing the transfer of separated components into component bags 14, 16. The squeezing system comprises a flexible diaphragm 98 that is secured to each container 84 so as to define an expandable chamber 100 in the cavity thereof. More specifically, the diaphragm 98 is dimensioned so as to line the bottom wall of the cavity 88 and a large portion of the lower wall of the cavity 88. The squeezing system further comprises a peripheral circular manifold 102 that forms a ring. Each expansion chamber 100 is connected to the manifold 102 by a supply channel 104 that extends through the wall of the respective container 84, close to the bottom thereof. The squeezing system further comprises a hydraulic pumping station 106 for pumping a hydraulic liquid in and out the expandable chambers 100 within the separation cells 78. The hydraulic liquid is selected so as to have a density slightly higher than the density of the densest of the components in the composite liquid to be separated (e.g. the red blood cells, when the composite liquid is blood). As a result, during centrifugation, the hydraulic liquid within the expandable chambers 100, whatever the volume thereof, will generally remain in the most external part of the separation cells 78. The pumping station 106 is connected to the expandable chambers 100, through a rotary seal 108, by a duct 110 that extends through the rotor shaft 70, through the bottom and lateral wall of the central container 74, and, radially outwardly where it connects to the manifold 102. The pumping station 106 comprises a piston pump having a piston 112 movable in a hydraulic cylinder 114 fluidly connected via the rotary seal or fluid coupling 108 to the rotor duct 110. The piston 112 is actuated by a brushless DC motor 116 that moves a lead screw 118 linked to a piston rod. The hydraulic cylinder 114 is also connected to a hydraulic liquid reservoir 120 having an access controlled by two valves 122a, 122b for selectively allowing the introduction or the withdrawal of hydraulic liquid into and from a reciprocating hydraulic circuit including the hydraulic cylinder 114, the rotor duct 110 and the expandable hydraulic chambers 100. A pressure gauge 124 is connected to the hydraulic circuit for measuring the hydraulic pressure therein.

The separation apparatus further comprises four sets of three pinch valves 128, 130, 132 that are mounted on the rotor around the opening of the central container 74. Each set of pinch valves 128, 130, 132 faces one separation cell 78, with which it is associated. The pinch valves 128, 130, 132 are designed for selectively blocking or allowing a flow of liquid through a flexible plastic tube, and selectively sealing and cutting a plastic tube. Each pinch valve 128, 130, 132 comprises an elongated cylindrical body 134 and a head 136 having a jaw 138 forming a gap that is defined by a stationary lower plate or anvil 140 and the jaw 138 movable between a "load" position, an "open" position, and a "closed" position. The gap is so dimensioned that one of the tubes 18, 32, 36, 46 of the bag sets shown in FIG. 1 can be snuggly engaged therein when the jaw is in the open position. The elongated body contains a mechanism for moving the jaw and it is connected to a radio frequency generator that supplies the energy necessary for sealing and cutting a plastic tube. The pinch valves 128, 130, 132 are mounted inside the central container 74, adjacent the interior surface thereof, so that their longitudinal axes are parallel to the rotation axis 68 and their heads protrude above the rim of the container 74. The position of a set of pinch valves 128, 130, 132 with respect to a separation bag 12 and the tubes 32, 36, 46 connected thereto when the separation bag 12 rests in the separation cell 78 associated with this set of pinch valves 128, 130, 132 is shown in dotted lines in FIG. 1. Electric power is supplied to the pinch valves 128, 130, 132 through a slip ring array 66 that is mounted around a lower portion of the rotor shaft 70.

Figure 3:
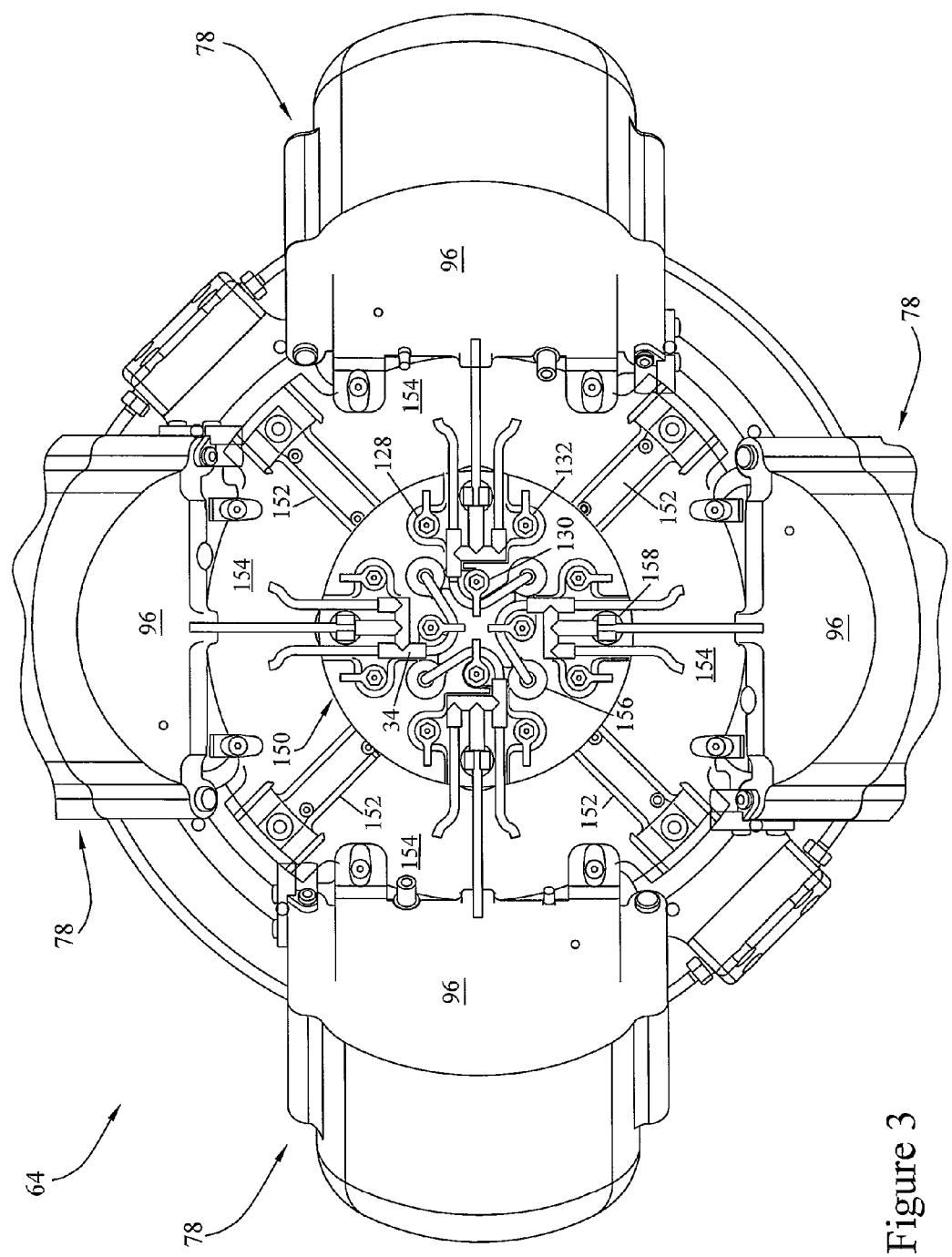
FIG. 3 is a top plan view of the separation apparatus of FIG. 2, showing at least part of a set of bags mounted thereon, showing an asymmetric manifold.
Figure 4:
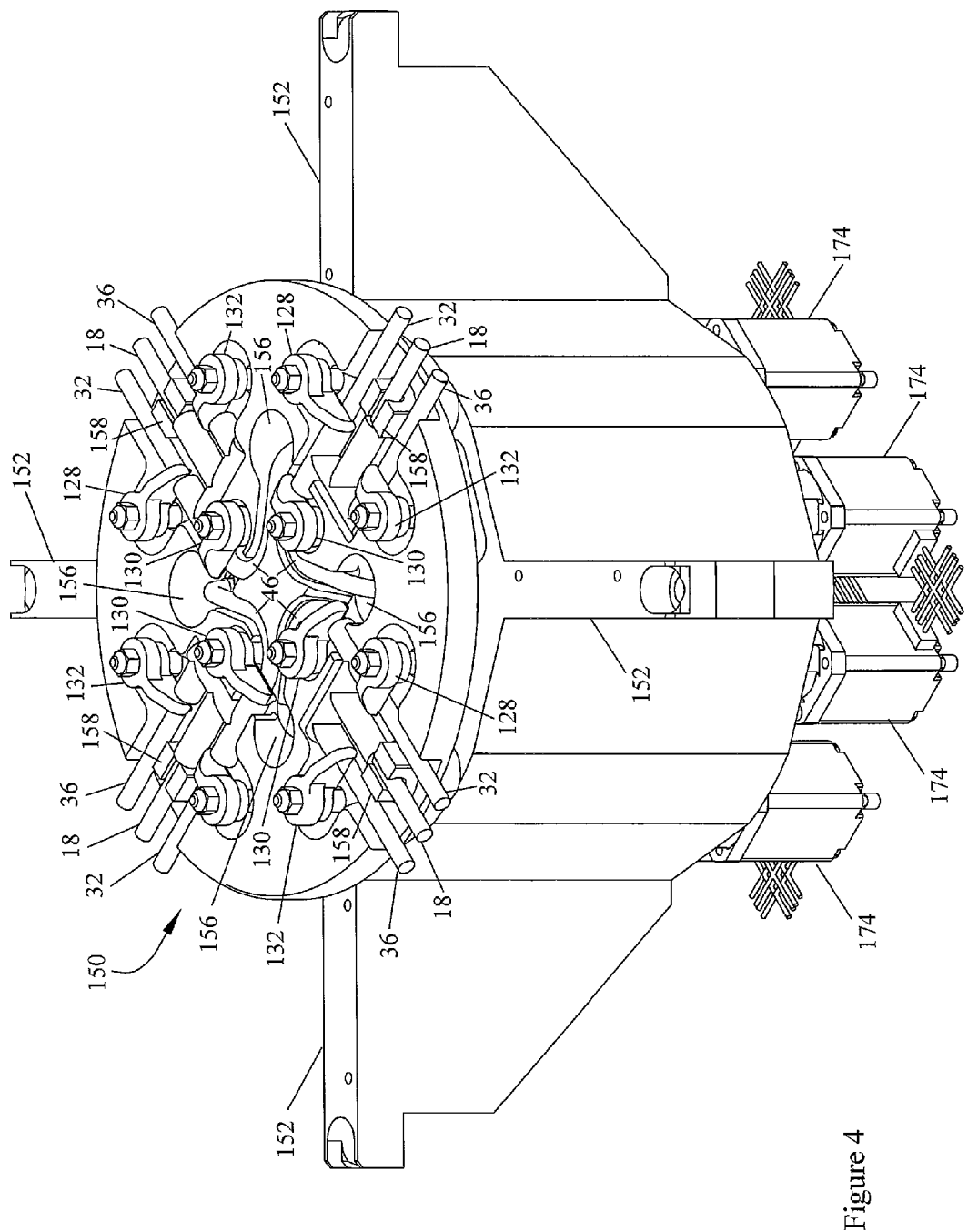
FIG. 4 is a perspective view of a core and set of bags according to FIG. 3.
Figure 5:
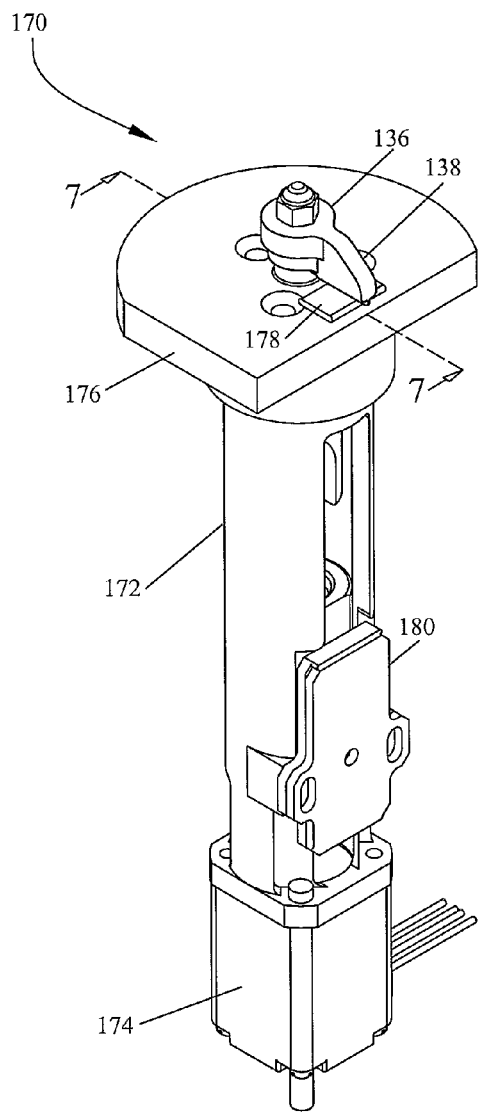
FIG. 5 is a perspective view of a valve.
Figure 6:
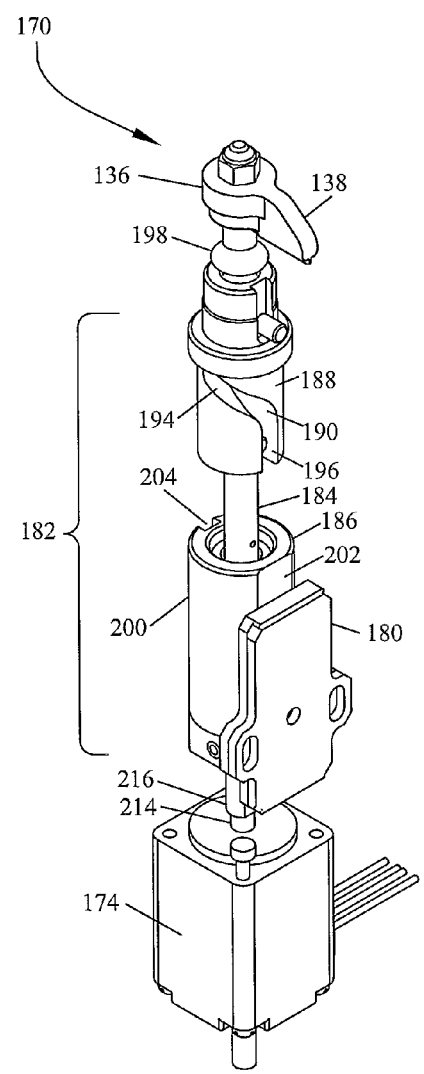
FIG. 6 is a perspective view of the valve of FIG. 5, with a housing removed.
Figure 7:
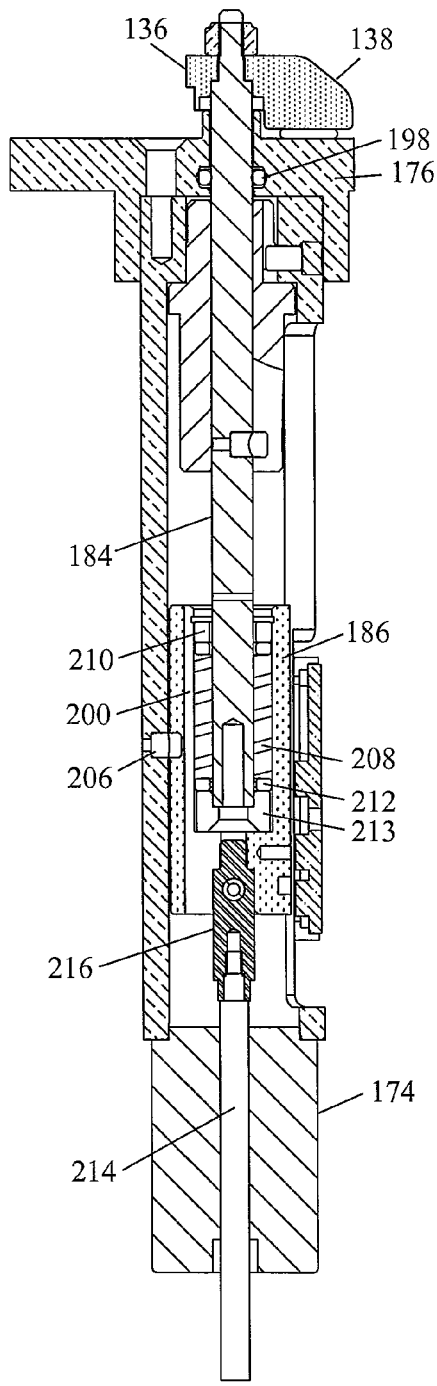
FIG. 7 is a cross sectional view of the valve of FIG. 5, taken along line 7-7.
Figure 8:
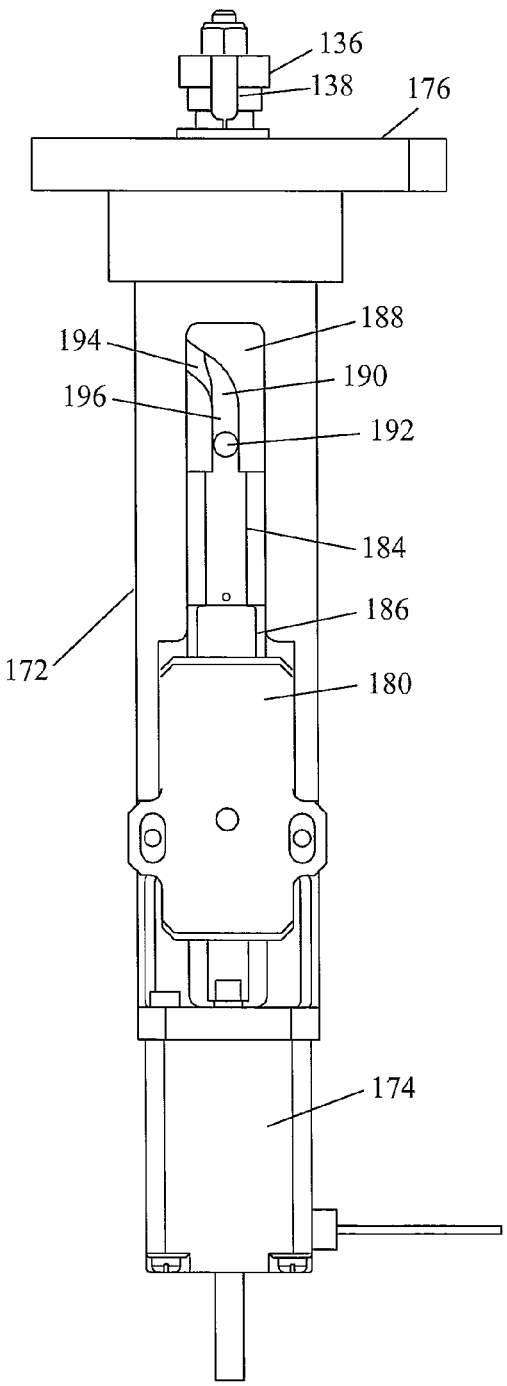
FIG. 8 is a plan view of the valve of FIG. 5.

Loading a multi-unit blood separator with a plurality of bag sets 10 can be time-consuming and repetitive. Rapid placement of tubes, such as tubes 18, 32, 36 and 46, is enhanced by the ability of the valve jaws in the "load" position to swing completely clear of a track or groove adapted to receive a tube. Accurate placement of the tubes is enhanced by the use of the asymmetrical manifold 34. The manifold is comprised of relatively rigid plastic and forms a junction for at least three, preferably four, flexible tubes. Connections for the tubes are asymmetrically spaced around the manifold. As shown in FIGS. 1, 3, and 4, an embodiment of the asymmetrical manifold 34 comprises an "E" configuration. The "E" configuration comprises a central rigid tube 166 with three stubs 168, 171, and 173 connected to tubes 32, 18 and 36, respectively. Diametrically across from the three stubs, a fourth stub 175 connects to tube 46 and thence to the auxiliary bag 44. The fourth stub 175 is asymmetrically placed along the tube 166. Because of the asymmetrical shape of the manifold, the manifold can be mounted in a shaped recess on the central core 150 in only one direction. Each of the tubes 18, 32, 36 and 46 of the bag set 10 will consequently be reliably mounted at the proper valve 128, 130, 132 or sensor 158 (described below).

The separation apparatus also comprises a controller 157 including a control unit (e.g. a microprocessor) and a memory unit for providing the microprocessor with information and programmed instructions relative to various separation protocols (e.g. a protocol for the separation of a plasma component and a blood cell component, or a protocol for the separation of a plasma component, a platelet component, and a red blood cell component) and to the operation of the apparatus in accordance with such separation protocols. In particular, the microprocessor is programmed for receiving information relative to the centrifugation speed(s) at which the rotor is to be rotated during the various stages of a separation process (e.g. stage of component separation, stage of a plasma component expression, stage of suspension of platelets in a plasma fraction, stage of a platelet component expression, etc), and information relative to the various transfer flow rates at which separated components are to be transferred from the separation bag 12 into the component bags 14, 16. The information relative to the various transfer flow rates can be expressed, for example, as hydraulic liquid flow rates in the hydraulic circuit, or as rotation speeds of the brushless DC motor 116 of the hydraulic pumping station 106. The microprocessor is further programmed for receiving, directly or through the memory, information from the pressure gauge 124 and from four pairs of photocells (described below) and for controlling the centrifuge motor 80, the brushless DC motor 116 of the pumping station 106, and the four sets of pinch valves 128, 130, 132 so as to cause the separation apparatus to operate along a selected separation protocol.

A first balancing means initially balances the rotor when the weights of the four separation bags 12 contained in the separation cells 78 are different. The first balancing means substantially comprises the same structural elements as the elements of the component transferring means described above, namely: four expandable hydraulic chambers 100 interconnected by a peripheral circular manifold 102, and a hydraulic liquid pumping station 106 for pumping hydraulic liquid into the hydraulic chambers 100 through a rotor duct 110, which is connected to the circular manifold 102. Under centrifugation forces, the hydraulic liquid will distribute unevenly in the four separation cells 78 depending on the difference in weight of the separation bags 12, and balance the rotor.

FIG. 3 shows a top plan view of the rotor 64. Four symmetrically spaced separation cells 78 (each with a lid 96) are shown surrounding a central core 150, which contains four sets of valves 128, 130, 132 and which supports the asymmetrical manifolds 34 and tubes of the bag sets 10. The core 150 is supported in the center of the rotor by a spider structure comprised of four radial support arms 152. The arms 152 define cavities 154 between a separation cell 78 and an adjacent set of valves 128, 130, 132 on the central core 150. The component bags 14 and 16 (for plasma and platelets respectively) and the red blood cell component bag 38, with its associated filter 40, are placed in the cavity 154 when the bag set 10 is loaded into the rotor 64. The collection and separation bag 12, which initially contains the collected unit of whole blood, is placed in the adjacent separation cell 78. The auxiliary bag 44, which may be used for temporary fluid storage, waste fluid collection or collection of a rare or small-volume blood component, is placed in a well 156 close to the axis of rotation 68 (see FIG. 2) of the rotor. The well 156 is closer to the axis of rotation than at least some of the valves associated with a single set 10 of bags. The well 156 may be cylindrical or rectangular to accommodate a rectangular bag 44, as shown in FIG. 1. The well is positioned such that the processing or primary separation bag 12 is located in a relatively high force region of the centrifugal field produced by the rotation of the rotor, while the component bags 14, 16 are located in a lower force region, and the smaller wash solution or discard bag 44 placed in the well would be in the lowest force region. By reason of bag placement in high, intermediate and low force regions of the centrifugal field, air will tend to collect in the wash bag 44 in the wel 156l. Moreover, a shorter line or tube can be used to connect the small bag to the entire bag assembly. The three placement zones aides in simplifying the bag assembly and makes the process of loading the bag assembly into the rotor easier.

FIG. 3 shows an asymmetric manifold 34 having an "E" configuration, which will be explained in greater detail below. For each set of valves, two outer valves 128, 132 are shown in "load" configuration, that is, the jaw of the valve does not extend over an adjacent tube, thereby allowing the manifold 34 and tubes to be installed in their proper configuration on the central core 150. For each set of valves, an inner or center valve 130 is shown in a position that could be either "open" or "closed", depending on the vertical position of the valve head and jaw, whereby flow in the adjacent tube is either permitted or impeded, respectively.

A tube sensor 158 is able to detect the presence or absence of liquid in the tube 18 as well as to detect blood cells in a liquid. Each sensor 158 may comprise a photocell including an infrared LED and a photo-detector. Electric power is supplied to the sensors 158 through the slip ring array that is mounted around the lower portion of the rotor shaft 70. In the process of separating blood into component parts, fluid components, such as plasma or platelets, are expressed out of the separation bag 12 in the separation cell 78 into component bags 14, 16 in the cavities 154. The sensor 158 may detect the presence of platelets or red blood cells. In response, the controller 157 may interrupt or change the processing for the particular set of bags where the new condition was sensed. Since the process of blood separation proceeds at different rates for different blood units, the volumes and weights of fluids in different bags and locations on the rotor will differ. A second balancing means 160 balances the rotor when the weights of the components transferred into the component bags 14, 16 in the cavities 154 are different. For example, when two blood donations have the same hematocrit and different volumes, the volumes of plasma extracted from each donation are different, and the same is true when two blood donations have the same volume and different hematocrit. The second balancing means comprises a balance assembly or ring 160, more particularly described in U.S. patent application Ser. No. 11/751,748, filed May 22, 2007, and incorporated herein by reference. The balancing apparatus of the separation apparatus comprises one or two balancing assemblies, each including a series of ponderous satellites or balls that can move freely on a specific circular orbit centered on and perpendicular to the axis of rotation of the rotor. The housing comprises a container for spherical ponderous satellites (balls) 162, which are housed in a cylindrical outer race, in which the balls slightly engage, and on which they roll, when the rotor rotates. The balancing means 160 comprises a plurality of balls. When the balls are in contact with each other, they occupy a sector of the ring of about 180 degrees. The balancing means 160 also comprises a damper or dampening fluid or element for providing resistance to the movement of the balls.

A valve unit 170 for valves 128, 130 and 132 is shown in FIGS. 5, 6, 7 and 8. The valve unit 170 comprises a valve housing 172 that is attached to a stepper motor 174 at the bottom and a non-conducting valve cover 176 at the top. The valve head 136 and jaw 138 protrude through the valve cover 176. In either the "open" or "closed" positions or if a weld is made, the jaw 138 is centered over a welding anvil 178. A position sensor 180 on the side of the valve housing 172 senses the vertical displacement of a shaft assembly 182 inside the housing and communicates that position information to the controller 157. The shaft assembly 182 comprises a shaft 184 that engages a spring-loaded coupling 186 at a distal end of the shaft 184, and a valve head 136 at a proximal end of the shaft. A combined cam and bearing 188 near the proximal end of the assembly has a guide slot 190 that engages a stationary pin 192. A spiral section 194 of the slot causes the head 136 and jaw 138 to rotate 90 degrees as the shaft 184 is displaced by the stepper motor 174. A straight section 196 of the slot causes the head 136 and jaw 138 to translate upward or downward without rotation. As a bearing, the combined cam and bearing 188 supports the shaft 184, allowing the shaft to translate up and down and to rotate. An O-ring seal 198 prevents fluids from entering the valve unit 170.

The spring-loaded coupling 186 comprises a casing 200 with a sensing surface 202 in magnetic contact with the position sensor 180 and a longitudinal slot 204 that engages a pin 206 such that the coupling 186 can move up and down within the valve housing 172, without rotating. A spring 208 within the casing 200 and surrounding the shaft 184, pushes against an upper end 210 of the casing 200 and against a washer 212 on the bottom end of the shaft 184. A bearing 213 below the washer allows the shaft 184 to rotate. A plunger 214 and joint 216 couple the stepper motor to the coupling 186 and translate the motion of the stepper motor to the coupling 186. As the coupling descends, the shaft 184 pulls head 136 down and the combined cam and bearing 188 turns the shaft 184, first rotating the jaw 138 as it descends and then lowering the jaw without rotation until the jaw contacts a tube, a position of the jaw called the "open" position. Further descent of the coupling 186 in response to the action of the stepper motor squeezes the jaw against the tube until the tube is closed and fluid flow is impeded. This action compresses the spring 208. If radio frequency energy is then directed through the jaw 138 and the electrically grounded welding anvil 178, the tube will melt and seal. The spring 208 expands during this process, lowering the jaw 138 towards the anvil 178 with a relatively constant pressure while maintaining the jaw in contact with the melting tube.

Figure 9:
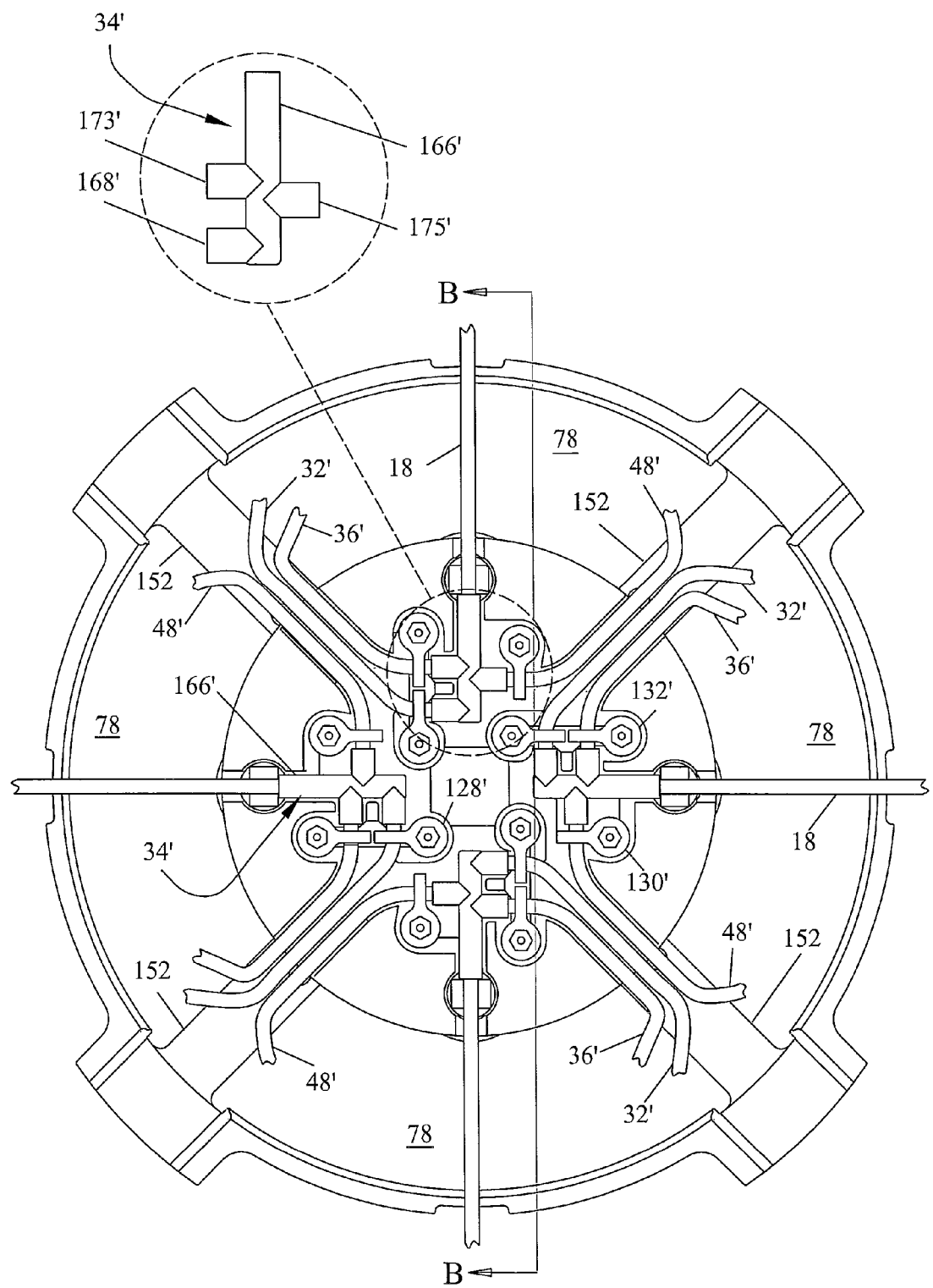
FIG. 9 is a top plan view of an alternative embodiment of a core and at least part of a set of bags mounted thereon, showing an alternative asymmetric manifold.
Figure 10:
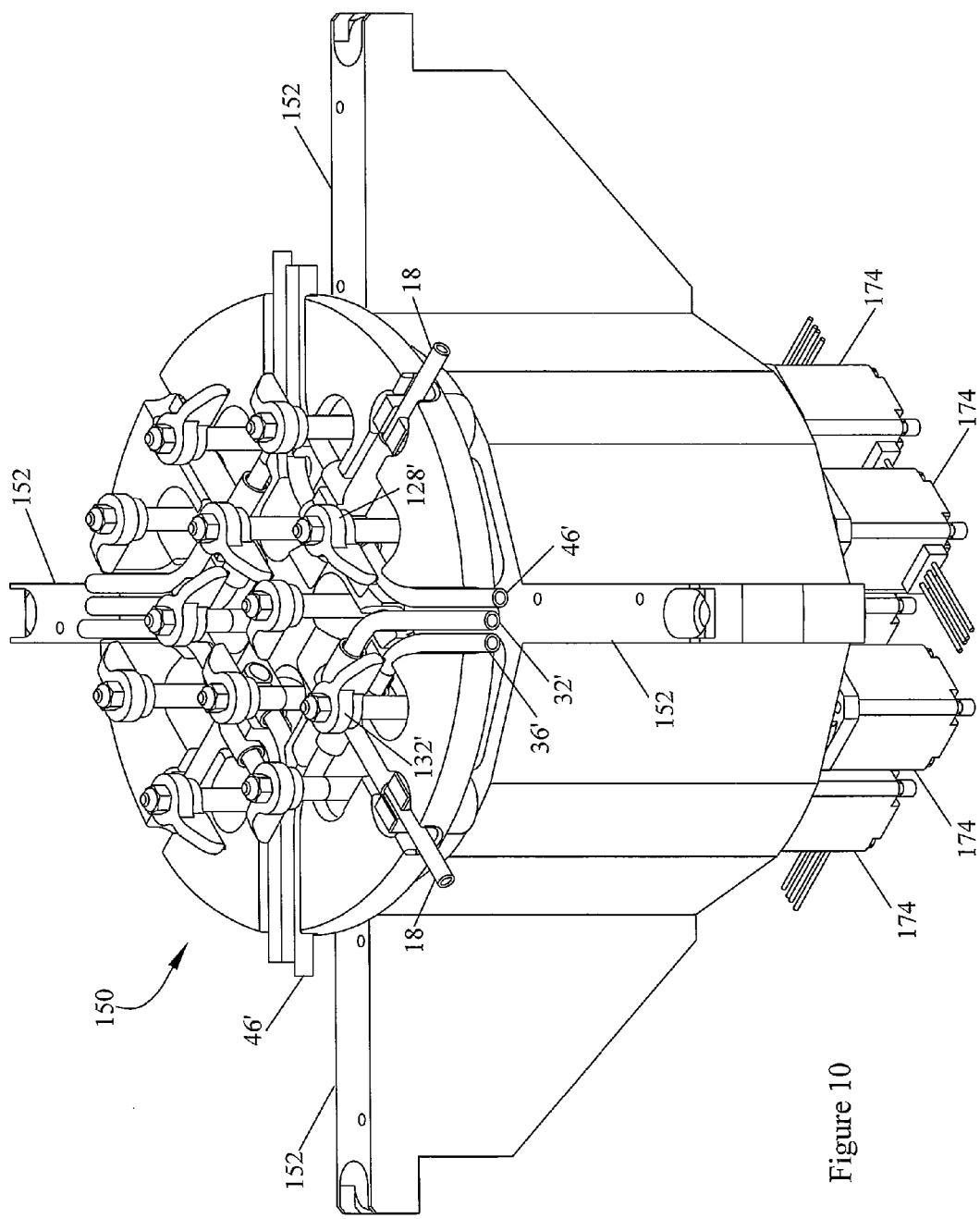
FIG. 10 is a perspective view of a core and set of bags according to FIG. 9.

An alternative embodiment of the central core 150' and asymmetrical manifold 34' is shown in FIGS. 9 and 10. In FIG. 10, valves are shown in a raised or "load" position, which allows an asymmetric manifold and tubes associated with a bag set to be quickly and accurately loaded into the apparatus. The alternative embodiment of the asymmetrical manifold 34' comprises an "F" configuration. The "F" configuration comprises a radial central rigid tube 166' connected directly to tube 18, which is the tube connected to the separation or whole blood bag. Three stubs 168', 173' and 175' connected to tubes 32', 36' and 46', respectively. The stub 175' connects to tube 46' and thence to the auxiliary bag 44. The stub 175' is asymmetrically placed along the tube 166' on the opposite side from stubs 168' and 173'. Once again, because of the asymmetrical shape of the manifold, the manifold can be mounted in a shaped recess on the central core 150' in only one direction. Each of the tubes 18, 32', 36' and 46' of the bag set will consequently be reliably mounted at their proper valves 128', 130', 132' or sensor 158. In this embodiment, all the bags 14, 16, 38, and 44, except the separation bag 12, are placed in the separation cells 78. This includes the wash solution/discard bags 44, which, in the previous embodiment, were placed in the centralized wells 156.

It is believed that the valve design described herein facilitates loading and unloading of blood bags and associated tubing and bag sets. In addition, the asymmetrical junction in the blood bag and tubing set inhibits errors when the bags and tubing sets are loaded into the device. Further, the well on a rotor near the axis of rotation, as described above, may be provided for receiving a relatively rare blood component, such as mesenchymal stem cells (MSC), or for receiving a fluid that can be used multiple times, such as a washing solution.

It will be apparent to those skilled in the art that various modifications can be made to the apparatus and method described herein. Thus, it should be understood that the invention is not limited to the subject matter discussed in the specification. Rather, the present invention is intended to cover modifications and variations.

The invention claimed is:

1. An apparatus for separating at least two discrete volumes of a composite liquid into at least a first component and a second component comprising
   a centrifuge rotor adapted to rotate about a rotation axis,
   at least one separation cell, adapted to receive a separation bag of a set of fluidly interconnected bags, said set comprising at least said separation bag containing a volume of composite liquid, and at least one component bag,
   a cavity adapted to receive at least said component bag,
   a plurality of valves, the valves being adapted to control fluid flow between parts of the set of interconnected bags, at least one of said valves comprising a jaw mounted on a shaft, said jaw being adapted to move from a load position allowing at least one tube to be placed adjacent said valve to an open position over said tube and from said open position to a closed position constricting fluid flow through said tube, and
   a controller electrically connected to said valves, said controller controlling the status of said valves, wherein said valves further comprise a cam mounted on said shaft, said cam guiding said jaw in a translating and rotating motion from said load position to said open position and in a translating motion from said load position to said closed position.

2. The apparatus according to claim 1, wherein said valves are placed to receive an asymmetrical manifold in a unique orientation.

3. The apparatus according to claim 2 wherein said rotor further comprises a recess shaped to receive said manifold in a unique orientation.

4. The apparatus according to claim 3 wherein said recess is adapted to receive at least three tubes which are coupled to said manifold.

5. The apparatus of claim 3 wherein said recess has an "E" shape.

6. The apparatus of claim 3 wherein said recess has an "F" shape.

7. The apparatus according to claim 1, wherein said jaw is adapted to apply radio frequency energy to an adjacent tube to seal said tube, and further comprising
   a spring coupled to said shaft and being adapted to maintain said jaw in contact with said tube as said tube is sealed.

8. The apparatus of claim 7, wherein said valve further comprises a cam mounted on said shaft, said cam guiding said jaw in a translating and rotating motion from said load position to said open position and in a translating motion from said load position to said closed position.

9. The apparatus according to claim 8, wherein said valves are placed to receive an asymmetrical manifold in a unique orientation.

10. The apparatus according to claim 9 wherein said rotor further comprises a recess shaped to receive said manifold in a unique orientation.

11. The apparatus according to claim 10 wherein said recess is adapted to receive at least three tubes which are coupled to said manifold.

12. The apparatus of claim 10 wherein said recess has an "E" shape.

13. The apparatus of claim 10 wherein said recess has an "F" shape.

* * * * *